United States Patent [19]

Krohn et al.

[11] 4,401,647

[45] Aug. 30, 1983

[54] RADIOLABELED NEOGLYCOPEPTIDES

[75] Inventors: Kenneth A. Krohn; David R. Vera; Robert C. Stadalnik, all of Sacramento, Calif.

[73] Assignee: The Regents of the University of CA, Berkeley, Calif.

[21] Appl. No.: 126,739

[22] Filed: Mar. 3, 1980

[51] Int. Cl.³ ............... A61K 43/00; A61K 37/02; A61K 49/02

[52] U.S. Cl. .................. 424/1.5; 424/9; 128/659

[58] Field of Search ............... 424/1, 1.5, 1.1

[56] References Cited

U.S. PATENT DOCUMENTS 4,010,251  3/1977  Green ........................ 424/1.5

OTHER PUBLICATIONS

Radiopharmaceuticals 2: Proceedings, 2nd International Symposium, (Mar. 19-22, 1979,) pp. 565-576, Sorenson, J. A. Ed.
David R. Vera et al., "Radioligands That Bind to Cel-1-Specific Receptors: Hepatic Binding Protein Fugands for Hepatic Scintigraphy".
American Journal of Roentgenology, vol. 132, No. 3, p. 492, Abstract 36 (1979) Vera, D. R. et al. "Radioligand . . .".
J. Biol. Chem. 253(17), pp. 6107-6110 (1978) Stowell, C. P. & Lee, Y. C.
"Am. J. Roentgenol, 132(3) p. 492(1979) Vera, D. R. et al.

Primary Examiner—Teddy S. Gron
Assistant Examiner—M. Moskowitz
Attorney, Agent, or Firm—Bertram I. Rowland

[57] ABSTRACT

Radiopharmaceuticals and method are provided for scintigraphic evaluation of the liver. The radiopharmaceuticals comprise a radionuclide (technetium) labeled neoglycoprotein which provides for specific binding of the radiopharmaceutical to hepatocytes and allows for accurate determination of rates of binding and release of Tc-99m to and from the liver. The observed rates may then be used to determine diseased states, conveniently using an appropriate algorithm for the calculation.

9 Claims, No Drawings

RADIOLABELED NEOGLYCOPEPTIDES

The invention described herein was made in the course of, or under, a grant from the National Institutes of Health.

BACKGROUND OF THE INVENTION

1. Field of the Invention

Diagnostic radiopharmaceuticals have been developed which have affinity for either the polygonal or reticuloendothelial cells of the liver. Iodinated rose bengal was a common hepatocyte imaging agent but suffered from having a long nuclear half-life and high energy nuclear emissions. More recently, technetium labeled hepatobiliary imaging agents have been developed but suffer from having short hepatocyte residence times and rapid excretion into the biliary tract. Among their shortcomings for liver imaging are visualization of the gall bladder and upper duodenum after maximal liver concentration is achieved, inability to obtain multiple views of the liver, wide patient variation in urinary excretion and reduced hepatic extraction and delayed biliary excretion in jaundiced patients.

The most common agent for clinical scintigraphic evaluation in the liver is Tc-99m-sulfur colloid (Tc-SC), which while finding wide use, lacks hepatic specificity and therefore has an inadequate ability to differentiate hepatic disease states.

2. Brief Description of the Prior Art

Krantz et al., Biochemistry 15 3963 (1976) describes a preparation of neoglycoproteins, particularly $\alpha$-amylase, hens egg lysozyme and bovine serum albumin with D-galactose and D-glucose. Vera, Krohn and Stadalnik presented a paper entitled "Radioligands that Bind to Cell-Specific Receptors: Hepatic Binding Protein Ligands for Hepatic Scintigraphy," at the proceedings of the Second International Symposium on Radiopharmaceuticals, Mar. 19–22, 1979 which describes the use of technetium-99m-galactosyl neoglycoalbumin for use as a radiopharmaceutical for hepatocyte binding. U.S. Pat. No. 4,010,251 reports the use of an asialoglycoprotein for visualizing liver and evaluating biliary function. Patents of interest describing the use of technetium-99m as a medical diagnostic radionuclide are U.S. Pat. Nos. 4,126,669; 4,104,366; 4,094,965; 3,872,226; and 3,466,361.

SUMMARY OF THE INVENTION

Radiopharmaceuticals and methods are provided for clinical scintigraphic evaluation of the liver employing a nonimmunogenic synthetic neoglycoprotein Tc-99m conjugate (Tc-99m NGP), particularly neoglycoalbumin Tc-99m conjugate (Tc-99m NGA) as the radiopharmaceutical. The compounds employed are specific for hepatocyte binding and allow for the determination of hemodynamic parameters, hepatocyte mass and hepatocyte metabolism. By determining the rate of binding and release of Tc-99m, the rates can be analyzed and related to liver disease states. Particularly, with an appropriate algorithm, the results can be correlated with various diseases of the liver.

DESCRIPTION OF THE SPECIFIC EMBODIMENTS

Compositions and method are provided for evaluating the presence of liver disease states by clinical scintigraphy. As a radiopharmaceutical, a product of the radionuclide Tc-99m and a synthetic neoglycoprotein, particularly neoglycoalbumin, is employed. The radiopharmaceutical is specific for hepatocytes, so that binding of the radiopharmaceutical to the liver can be directly related to hepatocyte mass, rather than reticuloendothelial cell agents, which primarily localize proportional to blood flow. By analysis of the rate of binding and release of the Tc-99m, conveniently employing a computer program, the data can be correlated with liver disease states.

Of particular clinical interest in studying the liver are such diseases as cirrhosis, hepatoma, metastasis, or other disease involving liver cellular function. Knowledge of a radiopharmaceutical's behavior at the cellular level is critical for proper accurate diagnostic interpretation and therapeutic management. The ideal radiopharmaceutical should allow for separation of the tracer kinetics into three phases: The hemodynamic phase would allow assessment of blood flow and vascularity. The binding phase would permit measurement of regional viability of the target cells based on chemical kinetic analysis. The release phase resulting from cellular metabolism and exocytosis of the tracer labeled products would provide additional physiologic and anatomic information.

The neoglycoproteins employed for the radiopharmaceutical which can provide the above information will be prepared synthetically from either naturally occurring or synthetic proteins. The proteins will generally be from about 20,000 to 500,000 molecular weight, more usually from about 30,000 to 150,000 molecular weight. They will be characterized by being substantially nonimmunogenic and having negligible biochemical affinity for receptor sites or physiological compartments other than hepatocytes, that is, they should not diffuse rapidly into extravascular or interstitial spaces or be rapidly excreted in the urine. Particularly applicable is human serum albumin although other proteins may be used, as well as some synthetic polypeptides such as polylysine.

The saccharides which are employed for modifying the protein may be mono- or polysaccharides, usually monohexoses, terminating in either D-galactose or D-glucose, particularly D-galactose. Conventional means can be employed for conjugating the sugars to the protein. Of particular interest is a method described by Lee et al., Biochemistry 15 3956 (1976) employing a thiopseudourea. The number of sugars may be varied widely, generally being at least about one per 20,000 molecular weight and usually not more than about one per 500 molecular weight, more usually not more than about one per 1,000 molecular weight. For albumin, there will normally be at least about 5 sugar groups, and not more than about 40 sugar groups, usually being from about 5 to 30 sugar groups.

When more galactose groups are coupled to the protein it increases the binding rate constant, $k_b$, for the NGP/receptor interaction.

An alternative to labeling the neoglycoprotein with Tc-99m directly is to attach a chelating agent to the protein. A number of chelating agents are described by Sundberg et al., J. of Med. Chem. 17, 1304 (1974). These include polyaminocarboxylate chelating agents, e.g. ethylenediaminetetraacetic acid. Chelating agents other than those employed by Sundberg include phosphonates (Costanovo et al., Article entitled "The Phosphate Moiety: Labeling with $^{99m}$Tc(Sn) After Synthetic Attachment to Diverse Biological Compounds," 1975, which is incorporated herein by reference.) The phosphonate may be coupled to the protein by means of a succinimide ester.

The number of chelating groups introduced will be at least stoichiometric with the number of neoglycoprotein molecules coupled and may be up to about 5 or more times molar excess.

The neoglycoprotein may be combined with Tc-99m by conventional means. The most common methods for reducing TcO$_4^-$ employ stannous ions as described by Eckelman et al., J. Nucl. Med. 12, 707 (1971) (the appropriate portions of which are incorporated herein by reference) or the electrolytic method described by Benjamin, International Journal of Applied Radiation and Isotopes, 20 187 (1969) (the appropriate portions of which are incorporated herein by reference). The particular method of reducing the technetium and binding it to the neoglycoprotein is not a critical element of the subject invention. The amount of Tc-99m will be at least 0.10 mCi/mg, will generally vary from about 1 to 100 mCi per milligram of neoglycoprotein, more usually from about 30 to 60 mCi/mg.

For in vivo scintigraphic analysis, the neoglycoprotein is combined with pertechnetate in appropriate proportions, and the pertechnetate reduced to Tc-99m to become bound to the neoglycoprotein. Other materials may be included which are pharmaceutically acceptable and do not interfere with diagnostic functions. These may include saline solutions, other sodium salts, acceptable buffers, or the like. Aseptic techniques and sterile, non-pyrogenic ingredients and containers are used at all times. After performing the reduction, the product may be sterilized if desired by passing through a biological filter of about 0.22μ pore size.

The neoglycoprotein can be conveniently provided in combination with sufficient stannous salt e.g. stannous chloride, that when combined with TcO$_4^-$-99m, the resulting product will have the desired amount of reduced technetium-99m. Usually, at least stoichiometric amounts of the stannous salt will be employed and up to about 50 mol percent excess. The amount of Tc-99m which becomes bound to the neoglycoprotein will vary due to the requirements for specific radioactivity. The Tc-99m will vary as to its activity concentration and the desired concentration of Tc-99m at the imaging site may also vary. Therefore, only general limitations as to the amount of reductant can be provided.

For administration, the product is injected aseptically into the blood stream, i.e. intravenously, the dosage range being between about 10 to 150 μCi/kg of body weight, usually being under about 50 μCi/kg body weight.

In evaluating the parameters involving the radiopharmaceutical the radionuclide monitoring need not be limited to the liver, but may also include or be substituted by monitoring of the urinary bladder, the precordium or carotid artery. As to one or more of these regions one would monitor at least one of the following factors: rate of uptake of the radionuclide; radioactive emissions; and radionuclide release. In this manner one follows the rate at which the radiopharmaceutical is transferred to a particular site, the binding capacity of the site and the rate of metabolism of the radiopharmaceutical.

The subject compounds demonstrate a number of desirable attributes for a radiopharmaceutical for hepatic imaging. First, their binding constants to hepatic binding protein (HBP) are lower than the hepatic blood flow so that membrane binding and not delivery by blood flow is the rate limiting step in the localization process. Second, the molecular processing of the subject compounds follows the scheme of delivery to the hepatic sinusoids, with binding of the subject compounds to the membrane receptor (HBP) at the rate $k_m$·[RP]·[HBP] (RP intends a radiopharmaceutical in accordance with the subject invention), where third, the RP-HBP complex will transfer the RP to lysosomes by endocytosis, resulting in catabolism of the substrate with subsequent release of the Tc-99m into the blood where it will be rapidly extracted by glomerular filtration.

The following mathematical equations are based on a model treating extrahepatic blood as compartment 1, hepatic blood as compartment 2, and hepatocyte as compartment 3:

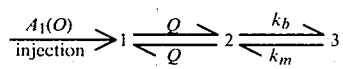

where Q=blood flow; $V_i$=compartment i volume; $A_i$=compartment i activity. If a region of interest is selected over a given lesion, the compartmental model predicts the following time activity equations resulting from the hepatic uptake of the Tc-99m-gal or glu NGP compound of the subject invention.

$$\frac{dA_1}{dt} = \frac{QA_2}{V_2} - \frac{QA_1}{V_1}$$

$$\frac{dA_2}{dt} = \frac{QA_1}{V_1} - \frac{QA_2}{V_2} + k_m A_3 - k_b[HBP] A_2$$

$$\frac{dA_3}{dt} = k_b[HBP] A_2 - k_m A_3$$

$A_1(O) = A_1(t) + A_2(t) + A_3(t)$
Liver activity = $A_2(t) + A_3(t)$
Precordial activity = $A_1(t)$ A computer fit of the measured hepatic uptake of the radiopharmaceutical with the above equations will yield a numerical solution to the kinetic parameters. When each curve is a response to a single set of alterations in model parameters governed by the properties of that disease state, a kinetic evaluation of each curve will lead to a unique predicted diagnosis. This can be achieved by determining the parameters for a number of individuals having particular diseased states which have been diagnosed by means other than the subject assay and relating the resulting parameters to the diagnosed diseased state.

The following examples are offered by way of illustration and not by way of limitation.

EXPERIMENTAL

The following describes the preparation of sterile non-pyrogenic Tc-99m-galactosyl neoglycoalbumin (Tc-99m-gal NGA).

2-Imino-2-methoxyethyl-1-thio-α-D-galactoside (prepared as described by Lee et al. Biochemistry 15 3956 (1976) IME-thiogalactose) was combined with a 20 mg/ml solution of human serum albumin (HSA) in 0.25 M Clark's borate buffer, pH8.5, in appropriate ratio to provide the desired sugar/albumin molar ratio. The solution was incubated at 37° C. for 1 hr. followed by transferring the solution under a laminar flow hood employing standard aseptic technique into a sterilized dialysis tube utilizing a disposable 0.22μ membrane. The reaction mixture is dialyzed against 0.15 M injectable saline overnight. Employing a 0.22μ filter, 25 mg aliquots of the dialysis product are placed into sterile 20 cc multidose vials, which are immediately lyophilized. The product (NGA) may then be analyzed for galactose units coupled per protein molecule.

In varying the mole ratio charged to the reaction mixture of IME-thiogalactose to albumin from about 10-600:1, the ratio of molecules of galactose conjugated to molecules of albumin varied from about 5 to 30.

Using aseptic technique, the lyophilized NGA is reconstituted by the addition of 2.5 ml of 0.15 M NaCl/HCl, pH1.3, followed by the addition of a predetermined volume Tc-99m-pertechnetate in normal saline solution. If the volume is greater than 0.5 ml, the pH of the solution is checked and readjusted to pH1.3 with dilute acid. After purging the vial with nitrogen for 10 mins., two one inch lenths of zirconium having been previously cleaned in acid are introduced as electrodes and connected to a constant power supply. The vial is inverted to immerse the electrodes and swirled to effect agitation of the solution. A constant current of 100 ma is then applied to the cell for 42 secs., the electrodes removed and the solution allowed to stand for 30 min. at room temperature while purging with nitrogen. The pH is then adjusted to neutrality by aseptic addition of 1 ml solution of bicarbonate.

The solution may then be filtered through a sterile 0.22μ membrane, followed by polyacetate electrophoresis at 250 volts to analytically separate the reduced Tc-99m, Tc-99m-NGA and pertechnetate. The yield of Tc-99m-NGA is ≧95% and the product can be used without further purification.

Following the above procedure, a product was obtained having 20 galactose residues per HSA macromolecule. The product was found to show no aggregation or colloid formation. Based on the results with chromatography with polyacrylamide P-300 Bio Gel the product would not localize in the liver by binding to reticuloendothelial cells.

The product was injected i.v. into the ears of several normal rabbits at a dosage of 0.05-0.5 mg/1.0-2.0 mCi for 2.5-3.0 kg rabbits. Blood samples were taken and the percent activity which was protein bound and blood clearance determined. Scintiphotos were taken to determine liver uptake kinetics. The blood clearance and liver uptake were plotted against time, and followed the anticipated kinetic equations described above.

The results can be regarded solely as a result of hepatocellular function. The Tc-99m-gal NGA exhibited 4-6% of the injected dose in the urinary bladder immediately following injection. Within 10 min. this number started to rise as labeled lysosomal products were extracted from the blood by glomerular filtration. Removal of the urine from rabbits after 30 min. showed this activity to be approximately 15% of the injected dose. In all of the in vivo rabbit trials, the Tc-99m-gal NGA showed a small degree of GI activity but in each experiment where the gall bladder was removed at 60 min, it was found to contain no radioactivity.

Based on the observed results, the products of this invention have the features needed for successful cell specific receptor based imaging of the liver. The radiopharmaceutical can be synthesized to produce the desired receptor affinity and its labeling is rapid, efficient and produces a ligand of high purity. The in vivo behavior is specific for the hepatocyte membrane and its uptake rate can be tailored to optimize the functional evaluation of the vascular, receptor binding, and metabolic dynamics.

Although the foregoing invention has been described in some detail by way of illustration and example for purposes of clarity of understanding, it will be obvious that certain changes and modifications may be practiced within the scope of the appended claims.

What is claimed is:

1. In a method for clinical scintigraphic hepatic imaging in a host, the improvement which comprises using as the imaging composition a composition comprised of a synthetic neoglycoprotein-Tc-99m conjugate of at least about 20,000 molecular weight and having at least one galactosyl or glucosyl residue per 20,000 molecular weight, said protein being nonimmunogenic to said host and exhibiting negligible biochemical affinity for receptor sites or physiological compartments other than the liver, wherein the amount of Tc-99m is at last 0.10 mCi/mg.

2. A method according to claim 1, wherein said glycoprotein is galactosyl serum albumin.

3. A method according to claim 1 or 2, which includes the steps of determining the rate of increase in the amount of Tc-99m in the liver and the rate of release of Tc-99m from the liver.

4. A method according to claim 1, wherein said glycoprotein is a galactosyl serum albumin, having from about 5 to 40 galactosyl groups.

5. A composition of matter comprising a galactosyl or glucosyl substituted serum albumin, having from about 5 to 40 galactosyl or glucosyl groups, combined with a reductant for pertechnetate sufficient to provide Tc-99m in an amount of from about 1 to 100 mCi/mg albumin.

6. A composition of matter according to claim 5, wherein said reductant is a stannous salt and said composition is galactosyl substituted.

7. A method for diagnosing liver disease states which comprises:
introducing into a host a predetermined amount of a radionuclide-containing radiopharmaceutical specifically binding to hepatocytes of the liver, said radiopharmaceutical comprising a neoglycoprotein-Tc-99m conjugate of at least about 20,000 molecular weight and having at least about one galactosyl or glucosyl residue per 20,000 molecular weight;
monitoring the radioactive emissions from at least one of the regions: liver, urinary bladder, precordium, or carotid artery, and determining data concerning at least two of (1) the rate of uptake of the radionuclide by said region; (2) the emissions from at least one site of said region; and (3) the release of the radionuclide from said region; and
analyzing the data as diagnostic of a liver disease state.

8. A method according to claim 7, wherein said radiopharmaceutical is Tc-99m-gal neoglycoalbumin.

9. A method according to any of claims 7 or 8, wherein at least one of said regions is said liver.

* * * * *